United States Patent
Ba-Abbad et al.

(10) Patent No.: US 9,174,890 B2
(45) Date of Patent: Nov. 3, 2015

(54) METHOD FOR CONVERSION OF CARBON DIOXIDE INTO HYDROCARBONS

(71) Applicant: KING SAUD UNIVERSITY, Riyadh (SA)

(72) Inventors: Mazen Abdullah Ba-Abbad, Riyadh (SA); Hany Al-Ansary, Riyadh (SA); Essam Al-Ammar, Riyadh (SA)

(73) Assignee: King Saud University (SA)

( * ) Notice: Subject to any disclaimer, the term of this patent is extended or adjusted under 35 U.S.C. 154(b) by 392 days.

(21) Appl. No.: 13/727,857

(22) Filed: Dec. 27, 2012

(65) Prior Publication Data

US 2013/0168966 A1 Jul. 4, 2013

(30) Foreign Application Priority Data

Dec. 28, 2011 (EP) ..................................... 11195918

(51) Int. Cl.
| | |
|---|---|
| *C07C 27/00* | (2006.01) |
| *C07C 1/04* | (2006.01) |
| *F01D 1/00* | (2006.01) |
| *C10G 2/00* | (2006.01) |

(52) U.S. Cl.
CPC ................ *C07C 1/0495* (2013.01); *C10G 2/32* (2013.01); *F01D 1/00* (2013.01)

(58) Field of Classification Search
CPC .............. C07C 1/00; C10G 2/30; C10G 2/32; C10G 2/50; C01B 3/00; C01B 3/06; C01B 13/0203
USPC ............................................ 518/703; 290/52
See application file for complete search history.

(56) References Cited

U.S. PATENT DOCUMENTS

| | | | |
|---|---|---|---|
| 4,184,852 | A | 1/1980 | Russ |
| 6,375,832 | B1 | 4/2002 | Eliasson et al. |
| 7,459,890 | B2 | 12/2008 | Baratto et al. |
| 7,596,952 | B2 | 10/2009 | Fradette et al. |
| 7,605,293 | B2 | 10/2009 | Olah et al. |

FOREIGN PATENT DOCUMENTS

WO    2004/028667 A1    4/2004

OTHER PUBLICATIONS

Extended European Search Report dated Jun. 20, 2012 for Appl. No. EP 11 19 5918.

*Primary Examiner* — Jafar Parsa
(74) *Attorney, Agent, or Firm* — Renner, Kenner; Arthur M. Reginelli

(57) ABSTRACT

The present invention relates to a method for converting carbon dioxide into hydrocarbons by reacting magnesium with carbon dioxide to obtain magnesium oxide and carbon, reacting the carbon with hot water steam to obtain hydrogen ($H_2$) and carbon monoxide, reacting hydrogen and carbon monoxide according to the Fischer-Tropsch method, or reacting the carbon obtained with earth alkaline metal oxide to obtain earth alkaline metal carbide and carbon monoxide, wherein the earth alkaline metal carbide is then reacted with water to obtain acetylene and earth alkaline metal hydroxide.

15 Claims, No Drawings

METHOD FOR CONVERSION OF CARBON DIOXIDE INTO HYDROCARBONS

The present invention relates to a method for conversion of carbon dioxide into hydrocarbons. Several methods are known in the art to convert carbon dioxide into several hydrocarbon materials.

U.S. Pat. No. 7,605,293 B2 discloses a method of reducing the carbon dioxide content of the atmosphere by recycling carbon dioxide and producing methanol using a reductive conversion of an available source of carbon dioxide that is present in or would otherwise be discharged into the atmosphere.

U.S. Pat. No. 7,596,952 B2 discloses a process for recycling carbon dioxide emissions from a fossil-fuel power plant into useful carbonated species, wherein the process comprises the steps of burning the fossil fuel, thereby generating heat and a hot exhaust gas containing carbon dioxide, and converting the heat into energy. This process is further characterized in that it comprises the steps of cooling the exhaust gas and biologically transforming the carbon dioxide contained in the cooled exhaust gas into carbonated species.

U.S. Pat. No. 7,459,590 B2 discloses a method for producing methanol and dimethyl ether using the air as the sole source of materials. The method is related to producing methanol by removing water from atmospheric air, obtaining hydrogen from the removed water, obtaining carbon dioxide from atmospheric air; and converting the carbon dioxide under conditions sufficient to produce methanol.

Further, U.S. Pat. No. 6,375,832 B1 discloses a method of transforming a normally gaseous composition containing at least one hydrogen source, at least one oxygen source and at least one carbon source into a normally liquid fuel, wherein said gaseous composition consists at least in part of carbon dioxide as said carbon source and said oxygen source, and of methane as said hydrogen source and as a second carbon source.

One disadvantage of the methods known in the art is that, if renewable energy, such as solar or wind energy, is utilized, the methods may not work efficiently, especially if solar wind energy is fluctuating or interrupted. Also, the known methods do not have forms of process energy recovery, i.e. thermal or photonic. Additionally, these methods may consume large amounts of fresh water, which is not widely available in many parts of the world. Also, the prior art methods may require complicated process controls and very expensive process equipment.

It is therefore an object of the present invention to provide a method for conversion of carbon dioxide into hydrocarbons which overcomes the difficulties and disadvantages of the prior art.

This object is achieved by a method for converting carbon dioxide into hydrocarbons, comprising the steps:
a) compressing air, optionally under removal of condensed water vapor, to a pressure of above 50 atmospheres, cooling the compressed air, preferably to about ambient temperature, separating carbon dioxide ($CO_2$) from oxygen ($O_2$) and nitrogen ($N_2$), storing carbon dioxide in a storage tank and preferably storing the heat generated during compression and/or cooling in a heat storage medium;
b) electrolyzing water to produce hydrogen ($H_2$) and oxygen ($O_2$), compressing the gases obtained and storing the heat generated during compression;
c) releasing carbon dioxide from the storage tank and reacting it with magnesium metal to produce magnesium oxide and carbon according to the following equation (1)

$$2Mg + CO_2 \rightarrow 2MgO + C \quad (1);$$

and either
d1) burning oxygen and hydrogen obtained in step b) in a hydrogen torch to obtain hot steam of a temperature of about 2.000-2.400° C., cooling the hot steam to a temperature of about 600-1.000° C. and then reacting the steam with carbon obtained in step c) according to the following equation (2)

$$H_2O + C \rightarrow H_2 + CO, \quad (2)$$

e1) Fischer-Tropsch reaction of CO and $H_2$ obtained in step d1) according to the following equation (3a)

$$nCO + (2n+1)H_2 \rightarrow C_nH_{(2n+2)} + nH_2O \quad (3a);$$

and/or
d2) reacting the carbon obtained in step c) with earth alkaline metal oxide MeO, preferably Ca or Mg, at a temperature of about 1.800-2.200° C. according to the following equation (4)

$$MeO + 3C \rightarrow MeC_2 + CO \quad (4)$$

e2) reacting the earth alkaline carbide obtained in step d2) with water to produce acetylene and/or acetylene derivatives; and/or
d3) reacting the carbon obtained in step c) with alumina according to the following equation (5)

$$2Al_2O_3 + 9C \rightarrow Al_4C_3 + 6CO \quad (5)$$

e3) reacting the aluminum carbide with water according to the following equation (6)

$$Al_4C_3 + 12H_2O \rightarrow 4Al(OH)_3 + 3CH_4 \quad (6);$$

and/or
d4) reacting the carbon obtained in step c) with beryllium oxide according to the following equation (7)

$$2BeO + 3C \rightarrow Be_2C + 2CO \quad (7)$$

e4) reacting beryllium carbide obtained in step d4) with water according to the following equation (8)

$$Be_2C + 2H_2O \rightarrow 2BeO + CH_4 \quad (8).$$

Step e2) produces acetylene, if Me=Ca according to the following equation:

$$CaC_2 + 2H_2O \rightarrow Ca(OH)_2 + C_2H_2 \text{(acetylene)}.$$

If in step e2) Me=Mg, methyl acetylene/propadiene is produced according to the following equation:

$$Mg_2C_3 + 4H_2O \rightarrow 2Mg(OH)_2 + C_3H_4.$$

The reaction between alumina and carbon in step d3) is carried out at a temperature of preferably above 2000° C., which heat can be taken from the oxygen and hydrogen combustion obtained in step d1). Further, the aluminum hydroxide obtained in step e3) can be converted into alumina by heating to a temperature of above 1000° C., which heat can for example be taken from the carbon monoxide and oxygen combustion. Further, also step d4), i.e. the reaction of beryllium oxide with carbon, is preferably carried out at a temperature of above 1500° C. Again, the required heat can be taken from reaction steps which release respective heat amounts.

In step b) the gases obtained are compressed to an optimum pressure, depending on the cost of the storage tanks. Further, the heat generated during compression can be also stored in the heat storage medium of step a).

In a preferred embodiment in step a) the energy for compressing air is provided from renewable energy sources. Renewable energy sources can be preferably wind and/or solar energy.

Even preferred, in step a) the air is compressed in multiple stages, wherein preferably at all stages of compression the compressed air/gases is/are cooled to ambient temperature.

In a further preferred embodiment, the air to be compressed in step a) is exhaust air from industrial plants, etc. having a higher content of $CO_2$ than atmospheric/ambient air.

Preferred, heat released when cooling the compressed air in step a) is stored in form of hot oil or molten salt.

In one embodiment, an intense light glow obtained in the reaction in step c) is transferred to photovoltaic cells for reduction of electricity.

In another embodiment, a cooling effect obtained when releasing $CO_2$ from its storage tank in step c) is used to cool the compressed air.

Preferably, the magnesium used in step c) is the form powder or billets.

The object is further achieved in that hot steam of a temperature of about 2.000-2.400° C. obtained in step d1) is transferred to a CaO wick to produce light which is then transferred to photovoltaic cells for producing electricity, method according to any of the preceding claims, wherein the hot steam of a temperature of about 2.000-2.400° C. obtained in step d1) is transferred to a CaO wick to produce light which is then transferred to photovoltaic cells for producing electricity, thereby cooling the steam to a temperature of about 600-1.000° C.

Preferably, a cooling effect obtained when releasing $H_2$ and $O_2$ from storage tanks in step d1) is used to cool the compressed air.

Even preferred, hydrocarbons and water vapor obtained in step e1) are heat exchanged with compressed air, the compressed air is then expanded in a gas turbine that turns an electrical generator.

Also preferred, when heat exchanging the hydrocarbons and water vapor with compressed air is that condensed water obtained is used for a hydration of MgO to prepare $Mg(OH)_2$.

The object is also achieved by a method wherein the CO obtained in step d2) is combusted with oxygen to produce $CO_2$ which can be transferred to step a), wherein preferably excess heat is used to heat the compressed air which is expanded in a turbine to produce electricity, or, alternatively, the CO is transferred into step e1). Preferably, oxygen stored after electrolysis in step b) can be used.

In a preferred embodiment the heat produced in step e2) is used to heat compressed air, preferably before being expanded in a turbine to generate electricity.

In another preferred embodiment, each alkaline hydroxide obtained in step e2) is dehydrated to its oxide, preferably using heat of the carbon monoxide obtained in step d2).

Preferably, the inventive method comprises additional steps of:

ci) hydrating the magnesium oxide obtained in step c) to its hydroxide according to the equation (9)

$$MgO+H_2O \rightarrow Mg(OH)_2 \qquad (9);$$

cii) preparing hydrochloric acid by reacting chlorine gas with hydrogen gas.

$$H_2+Cl_2 \rightarrow 2HCl;$$

ciii) preparing magnesium chloride according to the following equation (10)

$$Mg(OH)_2+2HCl \rightarrow MgCl_2+2H_2O \qquad (10);$$

civ) heating the magnesium chloride obtained to its melting point and electrolyzing thereof $$MgCl_2 \rightarrow Mg+Cl_2;$$

cv) transferring the Mg obtained into step c), and preferably recycling the $Cl_2$ obtained into the step ciii) of preparing hydrochloric acid.

Finally, the chlorine gas obtained is heat exchanged with the compressed air in step a) which is then expanded into a turbine to produce electricity.

In an also very preferred embodiment of the inventive method, the oxygen ($O_2$) and nitrogen ($N_2$) as received in the separation step a) of the inventive method, can be also further processed.

In this regard, it is preferred either ia) reacting oxygen with earth alkaline metal Me, preferably Mg and/or Ca, according to the following equation:

$$Me+O_2 \rightarrow MeO$$

ib) using the temperature released in step b1) to further react $N_2$ and $O_2$ according to the following equations:

$$N_2+O_2 \rightarrow 2NO$$

$$2NO+O_2 \rightarrow 2NO+O_2 \rightarrow 2NO_2$$

$$3NO_2+H_2O \rightarrow 2HNO_3+NO$$

and/or iia) reacting $N_2$ obtained in step 1 with earth alkaline metal Me, preferably Mg and/or Ca, according to the following equations:

$$3Me+N_2 \rightarrow Me_3N_2$$

$$Me_3N_2+6H_2O \rightarrow 3Me(OH)_2+2NH_3.$$

Again, the intense light glow obtained in the reaction in step ia) can be transferred to a photovoltaic cell for production of electricity.

Further, the NO obtained in step ib) can be heat exchanged with the compressed air used in step a), the compressed air may be then expanded in a gas turbine that turns an electrical generator.

Preferably, step iia) can be carried out at a temperature of about 600-1.000° C.

More preferably, the earth alkaline metal hydroxides obtained in step iia) can be at least partly reacted with nitric acid obtained in step ib).

In alternative, the earth alkaline metal hydroxides obtained in step iia) can be at least partly reacted with hydrochloric acid according to the following equation $$Me(OH)_2+2HCl \rightarrow MeCl_2+2H_2O$$

wherein the earth alkaline metal chloride to in then heated its melting temperature and electrolyzed $$MeCl_2 \rightarrow Me+Cl_2,$$

wherein optionally hydrochloric acid is then prepared by reacting the chlorine gas with hydrogen gas according to the following formula:

$$H_2+Cl_2 \rightarrow 2HCl.$$

In this regard it is also preferred that then the hot chlorine gas obtained is heat exchanged with compressed air of step a) which is then expanded in a gas turbine that turns an electrical generator, prior to recycling the chlorine gas to prepare hydrochloric acid.

A combination of a method for converting nitrogen into ammonia and/or nitrate with the inventive method for converting carbon dioxide at the number of benefits, for example improved flexibility, easy control to produce a variety of valuable hydrocarbon products as well as fertilizers. Further, especially when combining the method for converting carbon dioxide into hydrocarbons with production of ammonia and/or nitrate allows that the net reactions do not consume all of the oxygen gas, so that the system actually produces oxygen. In case that the compressed air contains suitable amounts of a moisture so that the water vapor is sufficient to form the hydrocarbons, the combined system then only needs $CO_2$, but will produce $O_2$.

Again, a portion of the process heat, either for a single process or for a combination, can be used to distill sea water with little effect on the system efficiency since the water desalination requires low grade heat.

Surprisingly it was found, that the present invention provides a new method to convert atmospheric carbon dioxide into useful hydrocarbons that can be used as fuel (gasoline and diesel) or valuable petrochemicals consuming only energy which can come preferably from renewable resources. The inventive method is much more economic with renewable energy forms that are fluctuating and require energy storage, for example solar and wind energy. Additionally, this method works best when utilized to absorb carbon dioxide from exhaust flue gases that are rich in carbon dioxide, for example from power plants, biological digesters or ammonia manufacturing plants. The inventive method provides higher efficiency than other methods, as most of the process heat, photonic emissions and cooling effects (decompression cooling) can be recovered and recycled into the system. Also this method has a net effect of producing oxygen. All this is done in a simple way.

The inventive method simply comprises renewable energy collection and conversion systems with waste heat recovery; an energy storage subsystem (in the form of compressed air), which serves also as a simple carbon dioxide capturing system. Water vapor exists in considerable quantities in the exhaust gases of oil or gas fired power plants, so this water vapor can be condensed and utilized. Another energy storage unit is the water splitting unit that preferably uses renewable energy electricity to electrolyze water and produce hydrogen and oxygen. During air, oxygen, hydrogen gases compression, the heat generated is preferably extracted and stored in hot fluid medium to be used later to pre-heat the gases in processes and into turbine expansion to generate electricity; and chemical reactors that are coupled with energy recovery subsystems for thermal and photonic recovery.

The only core method inputs are carbon dioxide, water and heat (at suitable temperatures for each method step) and electricity. Magnesium (Mg), water, magnesium or calcium hydroxide and chlorine gas are substances utilized in the method which can be fully recycled.

The inventive method is very flexible and can be easily controlled to produce a variety of valuable hydrocarbon products.

Further, it shall be highlighted that there are no harmful rejects to the environment.

DETAILED DESCRIPTION OF THE INVENTION

Step a)

Preferably using renewable energy sources, air is compressed, preferably in multiple stages, until the final pressure is above 50 atmosphere. The air utilized may be preferably exhaust air having a higher content of carbon dioxide compared to atmospheric air, which may be also filtered from suspended solids. Preferably, during the first stages of compression condensed water vapor is removed. During compression a separation into carbon dioxide on the one hand and oxygen ($O_2$) and nitrogen ($N_2$) on the other hand can be achieved, wherein collected carbon dioxide can be transferred to a separate storage tank. In all stages of compression, the compressed gases are preferably cooled to ambient temperature, and the heat released is then preferably stored in a heat storage medium, such as hot oil, molten salt, etc. This stored heat in each medium should preferably match with process heat requirements needed during the inventive method.

Step b)

Also preferably from renewable energy sources energy is provided to perform the water electrolysis reaction to produce hydrogen and oxygen. In a preferred embodiment, both gases are compressed and stored, and the heat generated during compression is extracted and stored as given above for step a).

When enough amounts of hydrogen, oxygen, carbon dioxide and stored energy (compressed air and heat) are available, the following reaction steps can take place.

Step c)

In step c), carbon dioxide can be released from a storage tank and is then reacted with magnesium, which is preferably in the form of solid powder or billets. The magnesium oxidation reaction releases a very large amount of heat at temperatures as high as 3.300 K, and also a very high intensity light.

As pointed out above, the reaction produces an intense light glow which can be transferred to photovoltaic cells to produce electricity.

Further, the release of carbon dioxide from its storage tank will cause the pressure and temperature to decrease. This cooling effect can be used to cool the compressed air tank utilized in step a), which will allow the gaseous carbon dioxide in the tank to return into liquid state and separates at lower pressure which allows then separation from the remaining gaseous components of the air utilized.

The reaction of step c) can be advantageously carried out by passing carbon dioxide through holes of a Mg holding tray. Above that tray photovoltaic cells can be arranged to convert the intense light glow obtained by this reaction into of electricity.

Step d1)

Before the reaction of step d1) is started, it is preferred that the stored oxygen and hydrogen are released and allowed to burn in a hydrogen torch to a high temperature. Very hot steam is formed which can be used to heat CaO (wick) to a temperature of around 2.400° C. to produce light. This type lightning was used before the introduction of electrical lamps and is called "lime light" which produces very intense light glow which photovoltaic cells can transfer into electricity. For step d1) therefore photovoltaic cells can be preferably formed into the walls of a chamber containing preferably a CaO wick, wherein the photovoltaic cells are shielded by quartz for protection against the hot steam.

While hot steam is introduced into such a chamber for producing CaO light at a temperature of about 2.400° C., the hot steam leaving this chamber only has a temperature of about 600 to 1.000° C. This steam may then be injected into the reaction product of step c), so that hot steam, preferably at a temperature of about 800° C., can react with carbon to obtain hydrogen ($H_2$) and carbon monoxide.

Preferably, this water gas reaction proceeds when all magnesium is oxidized. In this regard, it is to be emphasized that MgO will not react with the hot steam to form $Mg(OH)_2$, as at such high temperatures $Mg(OH)_2$ decomposes to MgO and $H_2O$.

Hydrogen and carbon monoxide obtained in this step are still of high temperature. Using a respective heat exchange equipment, this heat can be recovered and further used, for example in a magnesium recycling step, see below.

Hydrogen and carbon monoxide are then transferred to the further method step e1). It is further to be noted that also the reduction in the pressure of $H_2$ and $O_2$ storage tanks will decrease the tanks temperature, wherein this cooling effect can again be used to cool a compressed air holding tank, which will again allow the carbon dioxide to be separated as liquid.

Step e1)

In step e1) a well-known Fischer-Tropsch reaction is carried out at suitable temperatures, for example 150-350° C., and preferably in the presence of suitable catalysts. The Fischer-Tropsch reaction is well-known in the petrochemical industry and is used to produce hydrocarbon alkanes, such as gasoline and diesel, with proper control of pressure, temperature and catalysts. The formed hot hydrocarbons and water vapor are then allowed preferably to exchange heat with a compressed air, and the hot compressed air can be expanded in a gas turbine that turns an electrical generator. The condensed water can be also preferably used for the spontaneous MgO hydration, as explained below.

Step d2)

In an alternative, the carbon obtained in step c) can be reacted in step d2) with earth alkaline oxide while heating to about 2.000° C. to prepare earth alkaline carbide and carbon monoxide. While the earth alkaline carbide is further processed as described below, the resulting carbon monoxide can be, for example, combusted with any (stored) oxygen to produce more carbon dioxide that is then introduced into the reaction of step a), with the excess heat again suitable to heat the compressed air which is then expanded in a turbine to produce electricity. Alternatively, the carbon monoxide can be used in reaction e1) to produce hydrocarbons.

Step e2)

The earth alkaline carbide is then further processed by reacting spontaneously with water to produce earth alkaline metal hydroxide, and acetylene and/or acetylene derivatives. As is well known, acetylene and acetylene derivatives are valuable hydrocarbons which can be transformed (by hydrogenation) to ethylene or propylene, which are essential starting materials in plastics industry.

If calcium is chosen as earth alkaline metal, acetylene will be produced, while choosing magnesium as earth alkaline metal the reaction product would be methyl acetylene/propadiene $C_3H_4$.

The reaction of step e2) produces considerable amount of heat which can be used to heat compressed air before expanding in a turbine to generate electricity. The reactions of steps d2) and e2) can be carried out with magnesium and/or calcium.

The earth alkaline metal hydroxide obtained in step e2) can be easily dehydrated to its oxide (to be used again in step d2), for example by using the heat of the carbon monoxide obtained in step d2), at higher temperatures of about 500-550° C. according to the equation $$Me(OH)_2 \rightarrow MeO + H_2O$$

The resulting water vapor can be compressed to increase its temperature to around 800° C. to be used in the magnesium chloride melting in the following preferred Mg recycling reaction, and may later heat compressed air.

Step d3)

In an alternative, the carbon obtained in step c) can be also reacted with alumina at higher temperatures of above 2000° C. to produce aluminum carbide and carbon monoxide. The heat required for this reaction can be for example taken from the oxygen and hydrogen combustion.

Step e3)

The aluminum carbide obtained in step d3) can then be further reacted with water, preferably at room temperature, to produce aluminum hydroxide and methane.

In an additional step, the aluminum hydroxide may then be regenerated by heating to a temperature of above 1000° C. to produce alumina which can be then again reacted in step d3).

Step d4)

In a further alternative, the carbon obtained in step c) can be also reacted with beryllium oxide at a temperature of above 1500° C. Again, required heat can be taken from the oxygen and hydrogen combustion.

Step e4)

The beryllium carbide obtained can then be composed, preferably very slowly, with water, to produce beryllium oxide and methane.

In a most preferred embodiment, the inventive method comprises an additional process step, i.e. for recycling the magnesium oxide obtained in step c).

In a first step in this regard, the magnesium oxide is allowed to hydrate to its hydroxide using water that is a product of many reactions steps of the inventive method.

$$MgO + H_2O \rightarrow Mg(OH)_2$$

In a separate step, hydrochloric acid is prepared by reacting chlorine gas with (stored) hydrogen gas to form hydrogen chloride which, when adsorbing moisture, transforms into hydrochloric acid.

$$H_2 + Cl_2 \rightarrow 2HCl$$

Then, magnesium chloride can be produced according to the following equation.

$$Mg(OH)_2 + 2HCl \rightarrow MgCl_2 + 2H_2O$$

Finally, the magnesium chloride obtained is heated to melting temperature (750° C.), and an electrolysis is carried out to obtain magnesium (metal) and $Cl_2$.

$$MgCl_2 \rightarrow Mg + Cl_2$$

The hot chlorine gas can be allowed to exchange heat with compressed air which is then expanded into a turbine to generate electricity, and the then cooled chlorine gas can be recycled into the step for preparing hydrochloric acid.

If there is still process heat available which has not been consumed in the inventive method, this heat can be for example utilized to distil seawater with little effect on the system efficiency, since the water desalination requires only low grade heat.

The features disclosed in the foregoing description and in the claims may, both separately and in any combination thereof, be material for realizing the invention in diverse forms thereof.

The invention claimed is:

1. A method for converting carbon dioxide into hydrocarbons, comprising the steps:
   a) compressing air, optionally under removal of condensed water vapor, to a pressure of above 50 atmospheres, cooling the compressed air to about ambient temperature, separating carbon dioxide ($CO_2$) from oxygen ($O_2$) and nitrogen ($N_2$), storing carbon dioxide in a storage tank and storing heat generated during compression or cooling in a heat storage medium;
   b) electrolyzing water to produce hydrogen ($H_2$) and oxygen ($O_2$), compressing gases obtained and storing heat generated during compression;

c) releasing carbon dioxide from the storage tank and reacting with magnesium metal to produce magnesium oxide and carbon according to the following equation (1)

$$2Mg + CO_2 \rightarrow 2MgO + C \quad (1);$$

and d1) burning oxygen and hydrogen obtained in step b) in a hydrogen torch to obtain hot steam of a temperature of about 2000 to 2400° C., cooling the hot steam to a temperature of about 600 to 1000° C. and then reacting the steam with carbon obtained in step c) according to the following equation (2)

$$H_2O + C \rightarrow H_2 + CO, \quad (2);$$

e1) Fischer-Tropsch reaction of CO and $H_2$ obtained in step d1) according to the following equation (3a)

$$nCO + (2n+1)H_2 \rightarrow C_nH_{(2n+2)} + nH_2O \quad (3a);$$

or d2) reacting the carbon obtained in step c) with earth alkaline metal oxide MeO, Ca or Mg, at a temperature of about 1.800 to 2.200° C. according to the following equation (4)

$$MeO + 3C \rightarrow MeC_2 + CO \quad (4);$$

e2) reacting the earth alkaline carbide obtained in step d2) with water to produce acetylene and/or acetylene derivatives;

or d3) reacting the carbon obtained in step c) with alumina according to the following equation (5)

$$2Al_2O_3 + 9C \rightarrow Al_4C_3 + 6CO \quad (5);$$

e3) reacting the aluminum carbide with water according to the following equation (6)

$$Al_4C_3 + 12H_2O \rightarrow 4Al(OH)_3 + 3CH_4 \quad (6);$$

or d4) reacting the carbon obtained in step c) with beryllium oxide according to the following equation (7)

$$2BeO + 3C \rightarrow Be_2C + 2CO \quad (7); \text{ and}$$

e4) reacting beryllium carbide obtained in step d4) with water according to the following equation (8)

$$Be_2C + 2H_2O \rightarrow 2BeO + CH_4 \quad (8).$$

2. The method according to claim 1, wherein in step a) energy for compressing the air is provided from renewable energy sources.

3. The method according to claim 1, wherein in step a) the air is compressed in multiple stages, wherein at all stages of compression the compressed air/gases is/are cooled to ambient temperature.

4. The method according to claim 1, wherein heat released when cooling the compressed air in step a) is stored in form of hot oil or molten salt.

5. The method according to claim 1, wherein an intense light glow is produced from the reaction in step c) and is transferred to photovoltaic cells for production of electricity.

6. The method according to claim 1, wherein a cooling effect obtained when releasing $CO_2$ from said storage tank in step c) is used to cool the compressed air in step a).

7. The method according to claim 1, wherein the hot steam of a temperature of about 2000 to 2400° C. obtained in step d1) is transferred to a CaO wick to produce light which is then transferred to photovoltaic cells for producing electricity, thereby cooling the steam to a temperature of about 600 to 1000° C.

8. The method according to claim 1, wherein a cooling effect obtained when releasing $H_2$ and $O_2$ from storage tanks in step d1) is used to cool the compressed air.

9. The method according to claim 1, wherein hydrocarbons and water vapor obtained in step e1) are heat exchanged with compressed air, the compressed air is then expanded in a gas turbine that turns an electrical generator.

10. The method according to claim 9, wherein condensed water is used for hydration of MgO to prepare $Mg(OH)_2$.

11. The method according to claim 1, wherein the CO obtained in step d2 is combusted with oxygen to produce $CO_2$ which can be transferred to step a), wherein excess heat is used to heat the compressed air in step a) which is expanded in a turbine to produce electricity, or, alternatively, the CO is transferred into step e1).

12. The method according to claim 1, wherein heat produced in step e2) is used to heat compressed air, before being expanded in a turbine to generate electricity.

13. The method according to claim 1, wherein earth alkaline hydroxide obtained in step e2) is dehydrated to an oxide, using heat of the carbon monoxide obtained in step d2).

14. The method according to claim 1, comprising the additional steps:

ci) hydrating the magnesium oxide obtained in step c) to hydroxide according to the equation (9)

$$MgO + H_2O \rightarrow Mg(OH)_2 \quad (9);$$

cii) preparing hydrochloric acid by reacting chlorine gas with hydrogen gas, $$H_2 + Cl_2 \rightarrow 2HCl;$$

ciii) preparing magnesium chloride according to the following equation (10)

$$Mg(OH)_2 + 2HCl \rightarrow MgCl_2 + 2H_2O \quad (10);$$

civ) heating the magnesium chloride obtained to the melting point and electrolyzing thereof $$MgCl_2 \rightarrow Mg + Cl_2; \text{ and}$$

cv) transferring the Mg obtained into step c), and recycling the $Cl_2$ obtained into the step ciii) of preparing hydrochloric acid.

15. The method according to claim 14, wherein the chlorine gas obtained is heat exchanged with the compressed air in step a) which is then expanded into a turbine to produce electricity.

* * * * *